(12) United States Patent
Bopardikar et al.

(10) Patent No.: US 12,234,478 B2
(45) Date of Patent: Feb. 25, 2025

(54) METHOD OF AUTOLOGOUS PRIMARY HAIR FOLLICLES PREPARATION IN 3D CULTURE

(71) Applicant: REELABS PVT. LTD., Mumbai (IN)

(72) Inventors: Abhijit Bopardikar, Mumbai (IN); Oleksandr Kukharchuk, Mumbai (IN); Padma Priya Anand Baskaran, Mumbai (IN); Andrii Kukharchuk, Mumbai (IN); Sunil Pophale, Mumbai (IN); Rohit R. Kulkarni, Mumbai (IN)

(73) Assignee: REELABS PVT. LTD., Mumbai (IN)

( * ) Notice: Subject to any disclaimer, the term of this patent is extended or adjusted under 35 U.S.C. 154(b) by 666 days.

(21) Appl. No.: 16/629,402

(22) PCT Filed: May 3, 2019

(86) PCT No.: PCT/IB2019/053629
§ 371 (c)(1),
(2) Date: Jan. 8, 2020

(87) PCT Pub. No.: WO2019/215557
PCT Pub. Date: Nov. 14, 2019

(65) Prior Publication Data
US 2020/0149005 A1    May 14, 2020

(30) Foreign Application Priority Data

May 7, 2018 (IN) .............................. 201821017071

(51) Int. Cl.
*C12N 5/071* (2010.01)
*G01N 1/28* (2006.01)

(52) U.S. Cl.
CPC ............. *C12N 5/0627* (2013.01); *G01N 1/28* (2013.01); *C12N 2500/00* (2013.01); *C12N 2500/30* (2013.01); *C12N 2501/11* (2013.01); *C12N 2501/115* (2013.01); *C12N 2501/117* (2013.01); *C12N 2501/12* (2013.01); *C12N 2501/125* (2013.01); *C12N 2501/15* (2013.01); *C12N 2501/165* (2013.01); *C12N 2501/17* (2013.01); *C12N 2501/25* (2013.01); *C12N 2501/734* (2013.01); *C12N 2501/998* (2013.01); *C12N 2506/1346* (2013.01); *C12N 2513/00* (2013.01); *C12N 2533/56* (2013.01)

(58) Field of Classification Search
CPC .. G01N 1/28; C12N 2500/00; C12N 2500/30; C12N 2501/11; C12N 2501/115; C12N 2501/117; C12N 2501/12; C12N 2501/125; C12N 2501/15; C12N 2501/165; C12N 2501/17; C12N 2501/25; C12N 2501/734; C12N 2501/998; C12N 2506/1346; C12N 2513/00; C12N 2533/56
See application file for complete search history.

(56) References Cited

U.S. PATENT DOCUMENTS

| | | | |
|---|---|---|---|
| 8,932,583 B2 * | 1/2015 | Mooney | A61K 39/001156 435/402 |
| 2004/0247573 A1 | 12/2004 | Kim et al. | |
| 2007/0237750 A1 * | 10/2007 | Naughton | A61K 31/715 514/762 |
| 2011/0305671 A1 * | 12/2011 | Armani | A61P 17/14 424/93.3 |
| 2017/0182095 A1 * | 6/2017 | Terskikh | A61K 35/12 |
| 2017/0340771 A1 * | 11/2017 | Castro Feo | A61L 27/225 |
| 2018/0119093 A1 | 5/2018 | Kukharchuk et al. | |

FOREIGN PATENT DOCUMENTS

CN        106676060 A        5/2017

OTHER PUBLICATIONS

Driskell et al ("Hair follicle dermal papilla cells at a glance," J Cell Sci. Apr. 1, 20115; 124(8): 1179-1182) (Year: 2011).*
Dale et al ("Biochemical examination of fetal skin biopsy specimens obtained by fetoscopy: Use of the method for analysis of keratins and filaggrein," Prenatal Diagnosis, vol. 6,374 (1986) (Year: 1986).*
Wang et al ("Progress in Relevant Growth Factors Promoting the Growth of Hair Follicle," American Journal of Animal and Veterinary Sciences 7 (2): 104-111, 2012) (Year: 2012).*
Schneider et al ("The Hair Follicle as a Dynamic Miniorgan," Current Biology 19, R132-R142, Feb. 10, 2009) (Schneider) (Year: 2009).*
Fisher et al ("(Vascular endothelial growth factor and angiopoietin production by primate follicles during culture is a function of growth rate, gonadotrophin exposure and oxygen milieu," Human Reproduction, vol. 28, No. 12 pp. 3263-3270, 2013) (Fischer) (Year: 2013).*
Weterings et al ("Protein Biosynthesis in Cultured Human Hair Follicle Cells," Molec. Biol. Rep. 6, 153-158 (1980) (Weterings), (Year: 1980).*
Aoi et al ("Clinically applicable transplantation procedure of dermal papilla cells for hair follicle regeneration," J Tissue Eng Regen Med 2012;6:85-95) (Year: 2012).*
Limat et al ("Serial Cultivation of Single Keratinocytes from the Outer Root Sheath of Human Scalp Hair Follicles," J Invest Dermatol 87:485-488, 1986), (Year: 1986).*
PCT Search Report dated Sep. 10, 2019, Application No. PCT/IB19/53629.

* cited by examiner

*Primary Examiner* — Emily A Cordas
*Assistant Examiner* — Constantina E Stavrou
(74) *Attorney, Agent, or Firm* — The Dobrusin Law Firm, P.C.

(57) ABSTRACT

The present invention relates to a method for the preparation of autologous human primary hair follicles in 3D cultures, comprising the isolation of primary fetal follicles; isolation of the patient's hair follicle cells; isolation of skin cells of the patient's scalp; extraction of growth factors from fetal follicle cells; the fibrin gel creation that contains growth factors of fetal follicles; sandwich cultivation of patient's hair follicle cells and skin of the patients scalp on or into fibrin gel that contains growth factors of fetal follicles; separation from fibrin gel the patients primary hair follicles, which can be used to treat baldness as an autologous graft.

10 Claims, 15 Drawing Sheets

STAGES IN HAIR DEVELOPMENT

| Growth factors | pg/mL |
|---|---|
| HGF n = 14 | 43.91±11.84 |
| IGF-1 n = 14 | 432.6±65.76 |
| VEGF n = 14 | 26.55±10.43 |
| FGF-7 n = 15 | 121.90±37.10 |
| EGF n = 14 | 2.82±0.92 |
| SCF n = 14 | 440.70±19.52 |
| TGFβ1 n = 14 | 82.13±1.98 |
| TNFα n = 14 | 249.53±10.40 |
| ANGPT1 n = 14 | 12970.00±1062.39 |
| bFGF n = 14 | 9540.00±674.25 |
| VEGF-A n = 14 | 5360.00±381.13 |

(4a)  (4b)

(11a) ×100
(11b) ×100
(11c) ×200
(11d) ×200

(15a)  (15b)
(15c) ×200  (15d) ×200

METHOD OF AUTOLOGOUS PRIMARY HAIR FOLLICLES PREPARATION IN 3D CULTURE

FIELD OF THE INVENTION

This invention relates to the preparation of human primary hair follicles in 3D culture for therapeutic uses thereof.

BACKGROUND OF THE INVENTION

Hair loss also known as alopecia or baldness refers to a loss of hair from part of the head or body. The severity of hair loss can vary from a small area to the entire body. Hair loss in some people causes psychological distress. Common types include: male-pattern hair loss, female-pattern hair loss, alopecia areata, and a thinning of hair known as telogen effluvium. The cause of male-pattern hair loss is a combination of genetics and male hormones, the cause of female pattern hair loss is unclear, the cause of alopecia areata is autoimmune, and the cause of telogen effluvium is typically a physically or psychologically stressful event. Telogen effluvium is very common following pregnancy.

The management of alopecia involves use of medication or surgery. The medicines used in the alopecia are minoxidil, finasteride, and dutasteride; they typically work better to prevent further hair loss, than to regrow lost hair. The management of alopecia by surgery involves hair transplantation. Hair transplantation is usually carried out under local anaesthesia. A surgeon will move healthy hair from the back and sides of the head to areas of thinning. The procedure can take between four and eight hours, and additional sessions can be carried out to make hair even thicker. The conventional hair transplantation process suffers when there are not enough hairs in the non-bald areas. Also, in conventional hair transplantation, administration of hair follicle stem cells into the bald scalp zone has a very low efficiency since there are no required growth factors for the growth of new follicles in the skin of such a zone.

The emerging way of treatment and management of alopecia involves stem cell therapy. Stem cells are undifferentiated cells, which have the potential of differentiating into a various cell type. Stem cells are distinguished from other cell types by two important characteristics. First, they are unspecialized cells capable of renewing themselves through cell division, sometimes after long periods of inactivity. Further, under certain physiologic or experimental conditions, they can be induced to become tissue-specific or organ-specific cells with special functions. In some organs, such as the gut and bone marrow, stem cells regularly divide to repair and replace worn out or damaged tissues. In other organs, however, such as the pancreas and the heart, stem cells only divide under special conditions.

The hair follicle is a regenerating organ where stem cells allow for this massive large-scale renewal. The hair follicle is composed of an outer root sheath, an inner root sheath, and the hair shaft. The proliferating undifferentiated matrix cells give rise to the inner root sheath and the hair shaft and are surrounded by a dermal papilla of specialized mesenchymal cells. The dermal papilla instructs the formation of the follicle, but the characteristics of the follicle are acquired by epithelial information. The lower portion of the follicle goes through a growth cycle that involves the phases of anagen (active growth), catagen (destruction) and telogen (quiescence). These different phases last for varying time periods depending on the hair follicle location and function. The matrix cells proliferate rapidly during the anagen phase, migrate upwards then differentiate into the cell types of the inner root sheath and hair shaft. During the catagen phase, the lower follicle undergoes apoptotic death and the dermal papilla moves upwards until it reaches the area beneath the bulge. It remains there during telogen. Once the dermal papilla recruits stem cells from the bulge, anagen begins a new and the follicle can regenerate through proliferation and differentiation.

The journal of "Investigative Dermatology" 1989 February; 92(2): page no. 278-82 entitled "Ectopic growth of mouse whiskers from implanted lengths of plucked vibrissa follicles" discloses method for transplanting whole or partial whisker follicles from adult mice to a site beneath the kidney capsule of syngeneic mice.

The journal "Cell" 2001 Jan. 26; 104(2): page no. 233-45 entitled "Morphogenesis and renewal of hair follicles from adult multipotent stem cells" discloses the upper region of the outer root sheath of vibrissae follicles of adult mice contains multipotent stem cells that respond to morphogenetic signals to generate multiple hair follicles, sebaceous glands, and epidermis, i.e., all the lineages of the hairy skin.

The journal "Cell" 2000 Aug. 18; 102(4): page no. 451-61 entitled "Involvement of follicular stem cells in forming not only the follicle but also the epidermis" discloses hair follicular stem cells, located in the bulge region, can give rise to several cell types of the hair follicle as well as upper follicular cells.

The journal "Cell" 1994 Mar. 25; 76(6): page no. 1063-73 entitled "Location of stem cells of human hair follicles by clonal analysis" discloses growth capacity of keratinocytes isolated from human scalp hair follicle.

The journal "Proceedings of the National Academy of Sciences of the United States of America" 1993 Aug. 1; 90(15): page no. 7391-95 entitled "Segregation of keratinocyte colony-forming cells in the bulge of the rat vibrissa" discloses the bulge is the reservoir of the stem cells responsible for the long-term growth of the hair follicle and perhaps of the epidermis as well.

The commercially available products and method known in the prior art for the management and treatment of alopecia suffers from several drawbacks results in non-patient compliance and failure in the treatment of alopecia. The medicines like minoxidil, finasteride, and dutasteride typically work better to prevent further hair loss, than to regrow lost hair. Conventional hair transplantation process suffers when there are not enough hairs in the non-bald areas.

Therefore, there is unmet need in the art to provide method of autologous primary hair follicles preparation in 3D culture and their use in the treatment of alopecia; for the transplantation of primary hair follicles grown in 3D culture according to present invention, it is sufficient to have few hair follicles of patient only. Also, when growing primary hair follicles in 3D culture, growth factors have already been used and the patient is being injected with primary hair follicles ready for hair growth. Thus, the method for the preparation of human primary hair follicles in 3D cultures, including the isolation of primary fetal follicles; isolation of the patient's hair follicle cells; isolation of skin cells of the patient's scalp; extraction of growth factors from fetal follicle cells; the creation of a fibrin gel that contains growth factors of fetal follicles; sandwich cultivation of patient's hair follicle cells and skin of the patient's scalp in a fibrin gel that contains growth factors of fetal follicles; separation from fibrin gel the patient's primary hair follicles, which can be used to treat baldness as an autologous graft, provides better patient compliance and success in the treatment of alopecia.

OBJECTS OF THE INVENTION

Accordingly, it is an object of the present invention is to provide method of preparation of autological primary hair follicles in 3D culture.

It is another object of the present invention to provide use of Fetal hair follicles and their growth factors in the method of preparation of autological primary hair follicles in 3D culture.

It is another object of the present invention to provide use of Mesenchymal stem cells from the hair follicles of the patient's scalp occipital zone in the method of preparation of autological primary hair follicles in 3D culture.

It is another object of the present invention is to provide Expansion of mesenchymal stem cells of hair follicles of the patient in 2D cultures.

It is another object of the present invention is to provide Translation of the multiplicated mesenchymal stem cells of the hair follicles and scalp skin cells of the patient's occipital zone into a 3D culture based on a fibrin gel which contain specific growth factors isolated from fetal hair follicles.

It is another object of the present invention is to provide Lysis of fibrin gel in 3D culture with plasmin after formation of primary hair follicles It is another object of the present invention is to provide Purification of primary hair follicles from components of the incubation medium and preparing the suspension of primary hair follicles for transplantation into the skin of the patient's scalp.

In another object of the present invention is to provide method of preparation of primary hair follicles in 3D culture which provides better patient compliance and success in the treatment of alopecia.

SUMMARY OF THE INVENTION

A first aspect of the present invention is to provide method of formation of autological primary hair follicles in 3D culture.

In another aspect of the present invention is to provide separation and extraction of fetal hair follicles growth factors which in vitro stimulate the formation of autological primary hair follicles in 3D culture.

In another aspect of the present invention is to provide isolation and expansion of mesenchymal stem cells from the hair follicles of the patient's scalp occipital zone in 2D cultures In another aspect of the present invention is to provide translation of the multiplicated mesenchymal stem cells of the hair follicles and scalp skin cells of the patient's occipital zone into a 3D culture based on a fibrin gel which contain specific growth factors isolated from fetal hair follicles.

In another aspect of the present invention is to provide Lysis of fibrin gel with plasmin after formation of primary hair follicles in 3D culture and purification of primary hair follicles In another aspect of the present invention is to provide suspension of primary hair follicles for transplantation into the skin of the patient's scalp.

DETAIL DESCRIPTION OF THE INVENTION

Figure 1:
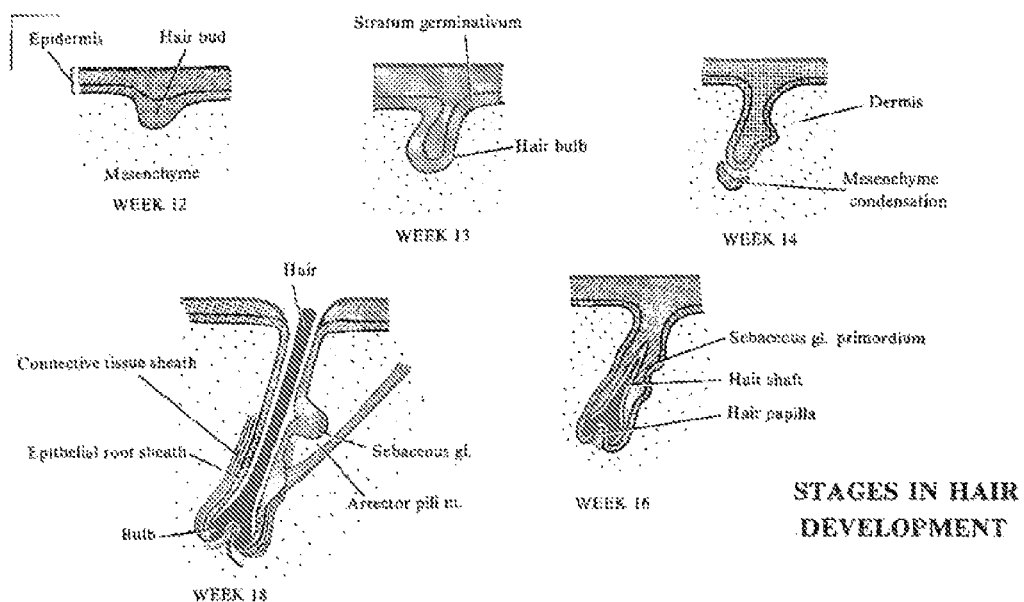
FIG. 1 demonstrates the development of the fetal follicle at different periods of gestation. We used for the extraction of cell growth factors of the fetal hair follicle at gestational age 18-20 weeks. At this time, all structures of the primary fetal follicle are already formed.

The present invention relates to the method of autologous primary hair follicles preparation in 3D culture for their use in the treatment of alopecia.

The term "autologous primary hair follicles" means that patients' hair follicles and pieces of scalp skin remove for separation of hair follicles mesenchymal stem cells and scalp skin cells, creation of primary hair follicles, and later given back to that same person.

Hair loss also known as alopecia or baldness refers to a loss of hair from part of the head or body. Common types include: male-pattern hair loss, female-pattern hair loss, alopecia areata, and a thinning of hair known as telogen effluvium.

The treatment of alopecia according to present invention may involve hair transplantation. Hair transplantation is a surgical technique that moves individual hair follicles from back of the scalp called the "donor site" to a bald or balding part of the scalp known as the "recipient site".

The hair transplantation according to present invention may involves isolation of stem cells from the hair follicles of the patient's scalp occipital zone, expansion of mesenchymal stem cells of hair follicles of the patient in 2D cultures, separation of scalp skin cells, translation of the mesenchymal stem cells of the hair follicles and scalp skin cells in to 3D culture, separation of primary hair follicles formed in 3D culture and preparing the suspension of primary hair follicles for multiple injections into the skin of the patient's scalp.

The term 2D culture according to present invention refers to research in tissue engineering, stem cells and molecular biology primarily involves cultures of mesenchymal stem cells of patients' hair follicles on flat plastic dishes. This technique is known as two-dimensional (2D) cell culture. The cells are put onto coated surfaces where they adhere and spread. Cell growth in 2D monolayers allows for access to a similar amount of nutrients and growth factors present in the medium, which results in homogenous growth and proliferation.

The term 3D culture according to present invention refers to an artificially created environment in which biological cells are permitted to grow or interact with their surroundings in all three dimensions. In 3D cell culture, cells attach to one another and form natural cell-to-cell attachments. The cells and the extracellular matrix that they synthesize and secrete in three dimensions is the natural material to which cells are attached. 3D cell culture allows cells in vitro to grow in all directions, similar to how they would in vivo.

Our experiments have shown that for the formation of the primary hair follicles of a patient in 3D culture, the presence in the fibrin gel growth factors that produce cells of fetal hair follicles is critical. If there are no such growth factors (as minimum special combination of concentration HGF, VEGF, FGF-7, EGF, SCF, TGF1$\beta$, TNF$\alpha$, ANGPT1, bFGF, and VEGF-A) in the fibrin gel, then the formation of the primary hair follicles from the cells of the patient (donor of mesenchymal stem cells of the hair follicles and scalp skin cells) does not occur.

Hair transplantation of primary hair follicles formed in 3D culture enables hair transplantation in case of 30 or few hairs present in the patient's non-bald areas; since the extracted stem cells of hair follicle grows and multiply through 2D and 3D culture to form multiplicated primary hair follicle which were purified and injected into the skin of the patient's scalp. Also, primary hair follicle growing in 3D culture utilizes the growth factors; therefore, the patient is being injected with primary hair follicles are ready for hair growth results in better patient compliance and success in the treatment of alopecia.

In hair transplantation, the methods of obtaining follicular units according to present invention may involve Follicular Unit Extraction (FUE).

Follicular unit extraction (FUE), also known as follicular transfer (FT), is one of two primary methods of obtaining follicular units, naturally occurring groups of one to four hairs, for hair transplantation. The other method is called strip harvesting. In FUE harvesting, individual follicular units are extracted directly from the hair restoration patient's donor area. This differs from strip-harvesting because, in strip harvesting, a strip of skin is removed from the patient and then dissected into many individual follicular units. The follicular units obtained by either method are the basic building blocks of follicular unit transplantation (FUT).

The Fox Test is carried out during follicular unit transplantation to see if a patient is suitable for direct extraction. This means checking to see if hair follicles are easy to remove and if they are suitable for implantation, without the risk of damage.

Therefore, before undertaking any patient for follicular unit extraction hair transplant, the surgeon ascertained whether the patient is a suitable candidate for FUE or not. In FOX test, the surgeon took out a few (about 100) grafts from the donor area and then evaluates how many complete/incomplete follicular units are extracted. If the extraction is easy and complete units are extracted, then the surgeon may go ahead with FUE; otherwise shift onto strip technique.

According to the ease and completeness of extracted grafts FOX test classified into five grades. Grade 1 is when intact follicular units literally pop out of the scalp or when there is only occasional transection of individual hairs in the unit. In Fox grade 2 patients, extraction may be relatively easy in the first session, but in subsequent procedures (when the donor area is slightly scarred) it becomes more problematic and the yield starts to decline. In these patients, the long-term yield can be compromised and planning extremely difficult. In FOX grade 3, the emergent angle is difficult. 74% of all the patients have FOX 1, FOX 2 or FOX 3. In Fox grade 4-5 (when it is almost impossible to predict the emergent angle), the yield is too low for the FUE procedure to be successful; here, the decision not to use FUE should be straightforward as the transection rate would be too high. If the patient is FOX-positive (grade 1-3), the surgeon may go ahead with FUE.

The method of formation of primary hair follicles in 3D culture according to present invention may include following steps:

Separation of fetal hair follicles in gestation term not less 18 weeks.

Extraction of fetal hair follicles growth factors.

Control of fetal hair follicles extract for biosafety.

Procedure of FUE.

The isolation of mesenchymal stem cells from the hair follicles of the patient's scalp occipital zone.

Expansion of mesenchymal stem cells of hair follicles of the patient in 2D cultures.

Separation of scalp skin cells of patient.

The translation of the multiplicated mesenchymal stem cells of the hair follicles and scalp skin cells of the patient's occipital zone into a 3D culture based on a fibrin gel which contain specific growth factors isolated from fetal hair follicles.

Lysis of fibrin gel with plasmin after formation of primary hair follicles or centrifugation gel for hair follicles separation.

Purification of primary hair follicles from components of the incubation medium and preparing the suspension of primary hair follicles for multiple injections into the skin of the patient's scalp.

The method for the preparation of human primary hair follicles in 3D cultures according to present invention comprises the isolation of primary fetal follicles; isolation of the patient's hair follicle cells; isolation of skin cells of the patient's scalp; extraction of growth factors from fetal follicle cells; the fibrin gel creation that contains growth factors of fetal follicles; sandwich cultivation of patient's hair follicle cells and skin of the patient's scalp on or into fibrin gel that contains growth factors of fetal follicles; separation from fibrin gel the patient's primary hair follicles, which can be used to treat baldness as an autologous graft.

The main requirement for fetal hair follicles is absence of bacteria, fungus and virus contamination. Biological safety of fetal hair follicles is provided by stringent control in all stages of production from procurement of anatomical material of dead fetus which was destroyed as the result of medical termination of pregnancy till the preparation of cells suspension for study or treatment.

Fetal Material Dispatch (Requirements to Donors): Inclusion criteria for selection of donor: the donor should be 18 yrs of age or above; the donor should be free from all the infectious diseases viz: HIV-1 & 2, HBV, HCV, CMV, VDRL; the duration of pregnancy should be between 18 to 20 weeks; the donor should undergo medical termination of pregnancy (MTP) and give her consent for the same. Exclusion criteria for donor: age of the pregnant women is less than 18 years; absence of "The Informed Consent for HIV Test", "The Informed Consent for MTP" or "The Informed Consent for the collection of the abortive material", of the pregnant women; period of pregnancy is above 20 weeks; pregnant women is detected with infectious diseases including HIV ½, HCV, HBV, CMV, VDRL; known history for intrauterine fetal death; if the aborted material is collected as a result of spontaneous abortion; known for clear signs of congenital anomalies or infection in fetus.

Screening Tests for donor of fetal hair follicles: All the screening tests for the selection of donor were performed as per the "Guidelines for Stem Cell Research and Therapy (2007)" and "Guidelines for Stem Cell Research (2013)" jointly issued by DBT & ICMR (India). The donors will be tested for the infectious diseases including HIV ½, HCV, HBV, CMV, and VDRL.

Medical Termination of pregnancy: MTP was performed by the recognized Gynecologist at the Gynecology Department of hospital. Only after the fulfillment of all the selection criteria, donor will be allowed to fill "The Informed Consent form for MTP". A separate consent form for MTP was provided by hospital. The "Informed consent form for donating the dead fetal tissue for research" was provided by Hospital, where the pre-abortion tests and MTP was carried out. Procuring abortive tissue would be implemented only by obstetrician-gynecologist and nurses of the medical institutions in which abortion was performed.

Contraindication for procuring of abortive tissue: Procurement of abortive tissue is not performed in cases where: age of the pregnant women is less than 18 years; absence of "The Informed Consent form for donating the abortive material" of the pregnant women; period of pregnancy is above 20 weeks; pregnant women is detected with infectious diseases including HIV ½, HCV, HBV, CMV, HTLV, VDRL; known history for intrauterine fetal death; known for clear signs of congenital anomalies or infection in fetus.

Collection of abortive material performed in sterile condition without changes in abortion technology, as permitted in India. Transportation of abortive material performed in special cryo-bags, which eliminates the possibilities of microbial contamination while transportation. Preliminary processing includes washing of anatomical material from blood and washed out solution taken for emergency microbial contamination analysis by the method of express endotoxin analysis.

Figure 2:
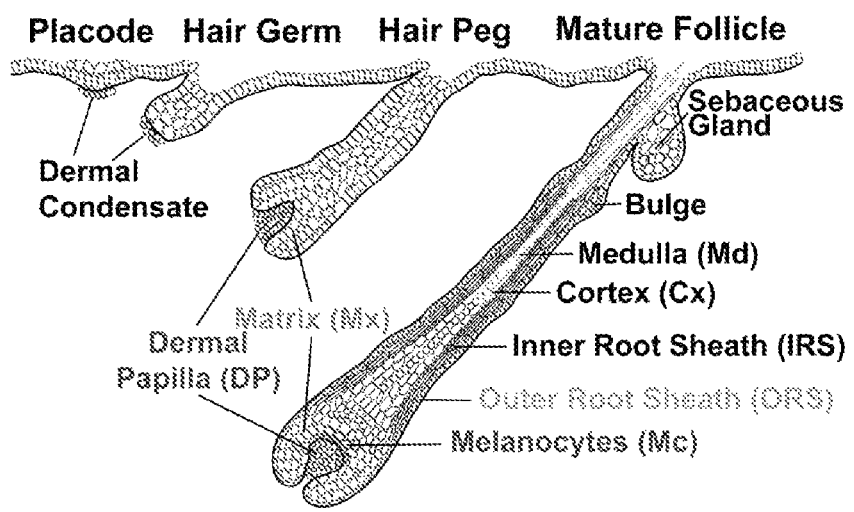
FIG. 2 shows the development of the hair follicle from the placode stage to the mature follicle. In our protocol, patient's hair follicle stem cells were used, which are located in the bulge. These cells were the mesenchymal component for the growth of the primary hair follicle. The skin cells of the patient's scalp were used as the epidermal component for the primary hair follicle development.

The choice of the gestational period of 18-20 weeks for the isolation of fetal follicles is due to the fact that in these periods the fetus primary hair follicles are already formed and are functionally active (FIG. 1). For the extraction of growth factors, all cells of the fetal hair follicles, both epidermal and mesenchymal origin, were used because dermal and mesenchymal cells take part in the formation of the hair follicle (FIG. 2).

Figure 3:
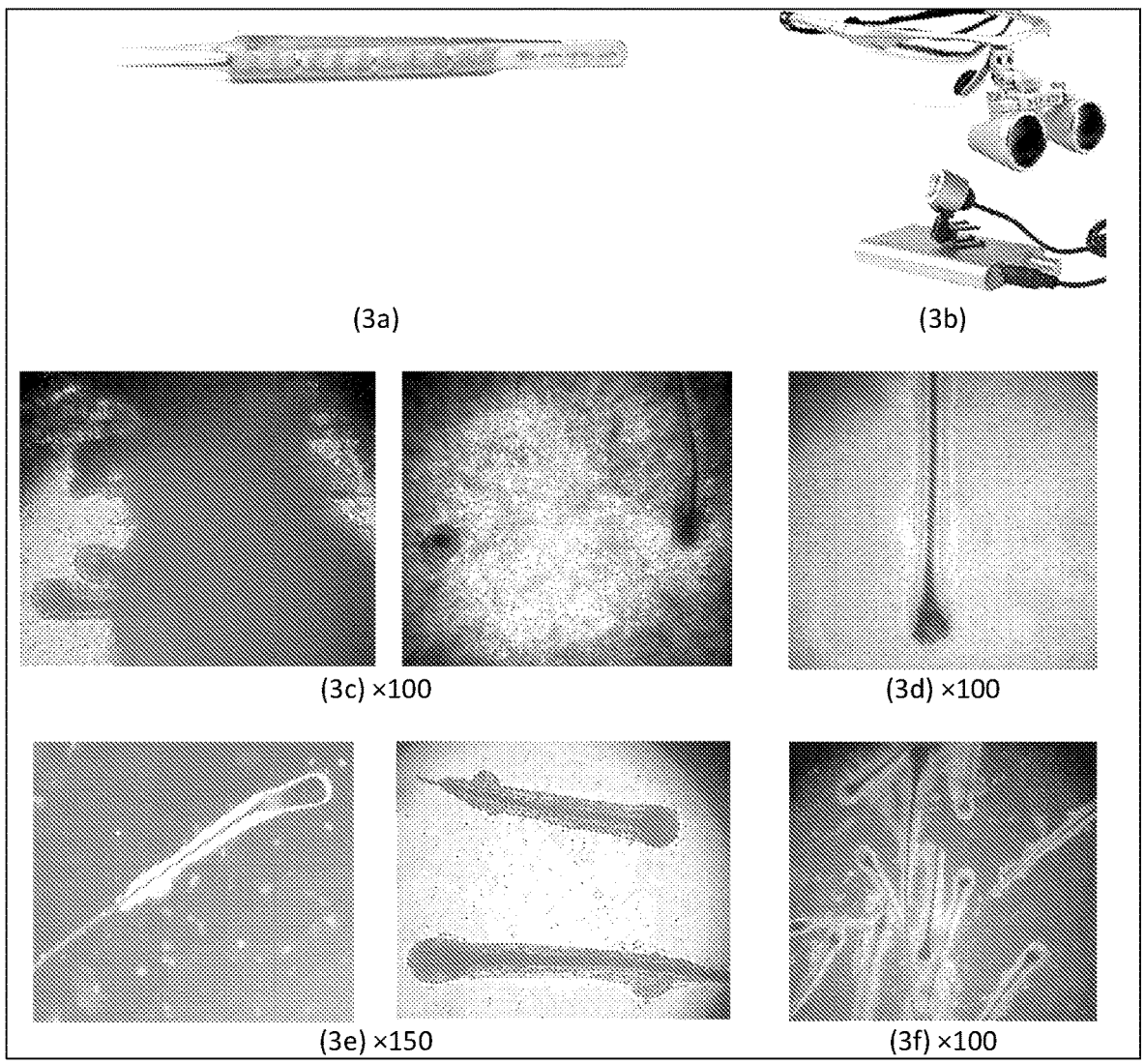
FIG. 3 demonstrates the protocol for the extraction of fetal hair follicles. Extraction is performed mechanically with tweezers (3a) using a dental loupe (3b) with magnification× 3.5-×4.0. (3c)—Scalp skin with fetal follicles. (3d)—Fetal follicle in the skin of the scalp. (3e)—Isolated fetal follicles. (3f)—Fetal follicles in the incubation medium.

The separation of fetal hair follicles from the skin of the fetal scalp (FIG. 3c, 3d) is performed mechanically using tweezers (FIG. 3a) and a dental loop with a magnification× 3.5×4.0 (FIG. 3b). Fetal follicles are easily and without damage released from the skin of the fetal scalp (FIG. 3e). The viability and integrity of the isolated fetal follicles is verified by short-term (48 hours) cultivation in DMEM (FIG. 3f).

Figure 4:
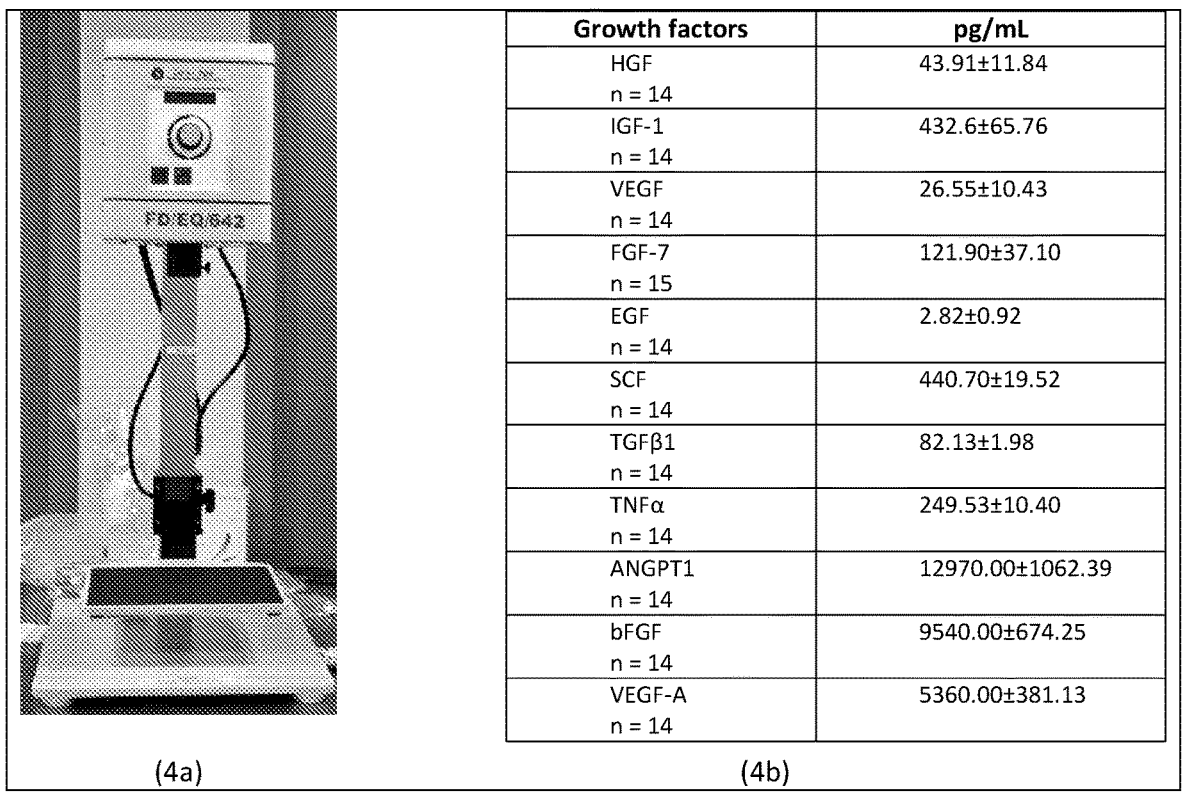
FIG. 4 shows a homogenizer for growth factors extracting from fetal hair follicles cells (4a), and concentration & level of growth factors in the extract of fetal hair follicles cells (4b): HGF—43.91±11.84 pg/ml (n=14); IGF-1—432.6±65.76 pg/ml (n=14); VEGF—26.55±10.43 pg/ml (n=14); FGF-7—121.90±37.10 pg/ml (n=14); EGF—2.82±0.92 pg/ml (n=11); SCF—440.70±19.52 pg/ml (n=14); TGFβ1—82.13±1.98 pg/ml (n=14); TNFα—249.53±10.40 pg/ml; ANGPT1—12970.00±1062.39 pg/ml (n=14); bFGF—9540.00±674.25 pg/ml (n=14); VEGF-A—5360.00±381.13 pg/ml (n=14).

Extraction procedure: The homogenization of the isolated fetal follicles was performed in a mechanical homogenizer (FIG. 4a) in DMEM. The homogenate was centrifuged (4000 rpm, 15 min). The supernatant was successively passed through filters with pore diameters of 100 and 40 µm. The content of growth factors (HGF, VEGF, FGF-7, EGF, SCF, TGF1β, TNFα, ANGPT1, bFGF, VEGF-A) in the filtrate was determined by enzyme immunoassay method (FIG. 4b).

Biosafety control: Part of fetal hair follicles extract were sent to an independent lab for biosafety control (study for bacterial sterility, contamination of viruses, fungus and transmission infections: HIV1/HIV2, HbsAg, HCV, HBV, HSV ½, CMV, Treponema pallidum, Toxoplasma gondii, Micoplasma, Ureaplasma, Chlamidii, EBV by means of polymerase chain reaction).

Figure 5:
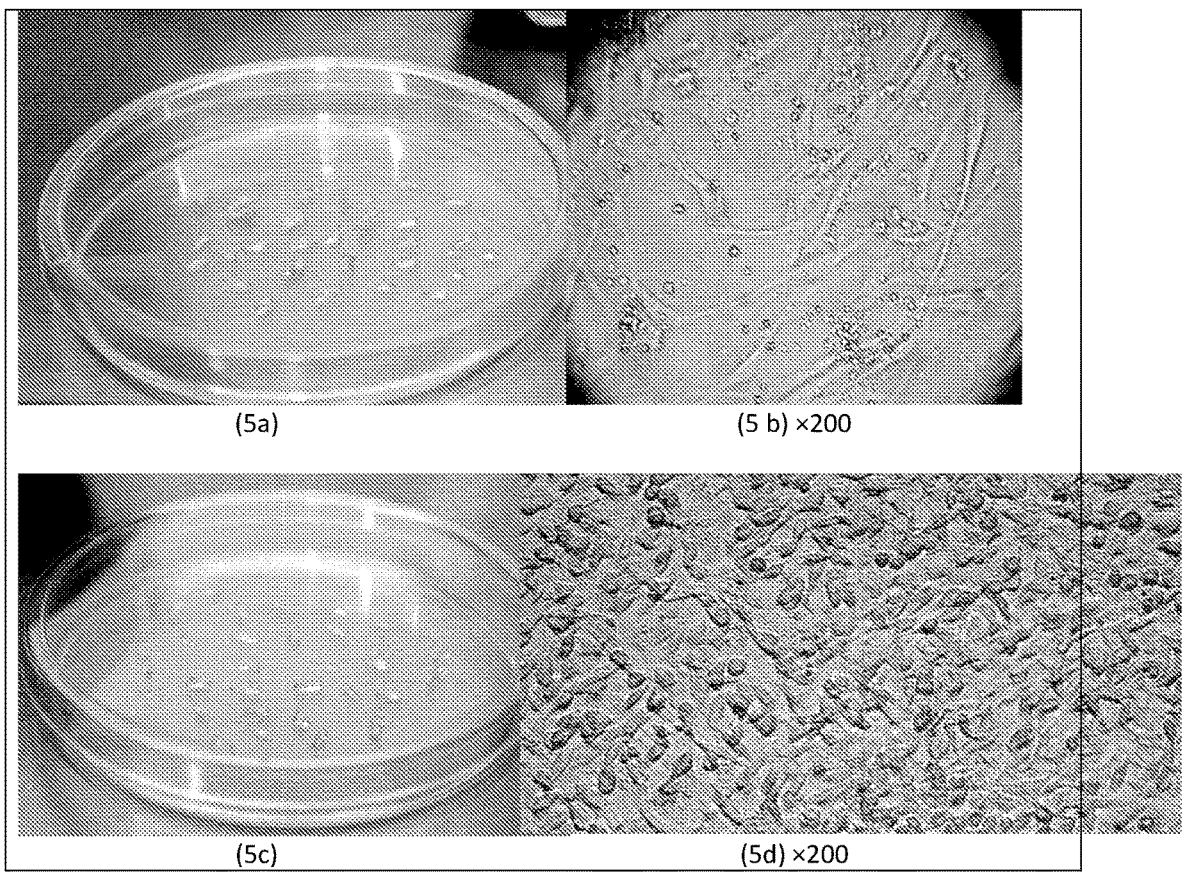
FIG. 5 demonstrates the patient's extracted hair follicles with scalp skin pieces (5a, 5c); the culture of the patient's separated scalp skin cells (5b), and the patient's hair follicle stem cells culture (5d).

Follicular unit extraction in patient-donor: Hair follicles are extracted from the back of head under local anesthesia with the help of special micro punches. On the day of surgery, the entire donor area from the back of the head is trimmed to 1-2 mm length. The patient lies in the prone position on the operating table. Local anesthesia with Xylocaine, 1% diluted with saline, is administered slowly over the entire donor area. The grafts are then extracted from the donor area with the help of 0.8-1 mm special micro punches. The extraction of follicles is done under 3.5-4.0× magnification. Step 1: With the sharp side of the micro punch, scoring of the scalp skin containing follicular unit is done. Step 2: Then dull side of the punch is introduced in the same area and is twisted to loosen the follicular unit. At the same time, the assistant applies counter traction to facilitate the penetration of the punch inside the dermis. Step 3: The assistant gently takes out the graft with the help of forceps. The extracted unit "scalp skin-hair follicles" are then preserved in cool saline (in 50.0 ml sterile tube). The extracted unit may consist of 1 to 2 hair follicles (FIG. 5a, FIG. 5c).

Procedure of isolation and expansion of mesenchymal stem cells from human hair follicles: Hair follicles of patient-donor collected in sterile container with normal saline and Gentamycin. Step 0. Carefully separate the scalp skin pieces from the hair follicle. Place the pieces of scalp skin in a Petri dish and place the Petri dish on ice. Step 1. Wash hair follicles with sterile PBS until nearly free from blood in 50 ml centrifuge tube. Step 2. Mince hair follicles with sterile scissors. Add 2 ml of 0.1% Collagenase type IV and 0.5 ml of 0.1% Dispase into the centrifuge tube for digestion. Incubate the sterile centrifuge tube in a 3° C. incubator for 1 hour. After incubation inactivate the collagenase and Dispase activity with 10% FBS. Filter the cells suspension after digestion using 100-micron cell. Centrifuge the filtrate at 1500 rpm for 10 minutes. Discard the supernatant and resuspend the pellet in DMEM for culturing. Step 3. Take one T25 cm2 flask and label as Hair follicles with date on the flask. Seed isolated cell suspension into T25 flask with DMEM (10% FBS) in a density of 5×104 cells/cm2. Incubated flask in 5% CO2 incubator with 95% humidity at 37° C. Change the Media twice in a week thereby removing the non-adherent cells along with used media. Step 4. After 12-15 days of incubation (70-80% confluency) subculture primary cell line. Discard the media and rinse with 1× PBS, then add 3 ml of Trypsin-EDTA solution (0.25%) and incubated at 37° C. for 3 min in a CO2 incubator. Step 5. Observe flask under inverted microscope for complete detachment of cells. Add fresh DMEM media with 10% FBS to inactivate Trypsin activity. Collect the cells into 50 ml centrifuge tube. Centrifuge the 50 ml centrifuge tube at 1500 rpm for 10 min at room temperature, discard the supernatant and resuspend the pellet in the Culture medium. Determined the cell count using hemocytometer. Step 6. Seed the cells in one T75 cm2 flask (0.5 Million cells per flask) and incubate at 37° C. in a 5% CO2 incubator. Change the media after three days. Observe flask for 70-80% confluency, follow the steps of cells culturing. Seed the cells in 3-4 T75 flasks with DMEM at a concentration of 0.5 million cells per flask and incubate at 37° C. in a 5% CO2 incubator. Change the media after three days. Step 7. After flasks reach 70-80% confluency, follow the steps of cells culturing. Seed cells into Hyper-flask (10-12 million cells per flask) with DMEM Medium (10% FBS) and incubate at 37° C. in a CO2 incubator. Change the media after twelve days. Regularly observe flask for full confluency (80-90%). Discard the media from the Hyper-flask, wash the flask with 1× sterile PBS. Add 50 ml of Trypsin EDTA solution and incubate in CO2 Incubator for 5 minutes at 37° C. Add 100 ml fresh DMEM media containing 10% FBS to stop the trypsin activity. Dispense the media containing cells into 50 ml centrifuge tubes and centrifuge at 1500 rpm for 10 minutes. Resuspend the pellets in sterile saline and pool the pellets. Centrifuge the tube at 1500 rpm for 10 minutes. Determine the cell count. Number of cells should be not less than 15 million per ml (FIG. 5d).

Procedure of cells isolation from patient-donor the scalp skin pieces: Transfer scalp skin pieces from Petri dish into Teflon Cells Homogenizer. After soft homogenization in DMSO fat and damaged cells removed from homogenate by centrifugation at 2700 rpm for 15 minutes. Then 4.0 ml of scalp skin cells suspension washed extensively with sterile Hanks solution. Extracellular matrix destroyed at 37° C. in Hank's solution with 1 mg/ml collagenase type I, and 2% of bovine albumin. After incubation of enzymatic activity, neutralized with Dulbecco media, containing 10% fetal bovine serum, and centrifuged at 1200 rpm for 10 minutes. The resulting scalp skin cells fraction transferred into a 160 mM solution of ammonium chloride and incubated at room temperature for 10 min for destruction of red blood cells and filtered through 200 μm nylon mesh. Ready skin scalp cells suspension (FIG. 5b) cryopreserved for long-term storage in liquid nitrogen after adding to cell suspensions the solution of 10% DMSO (volume of 1:1).

Figure 6:
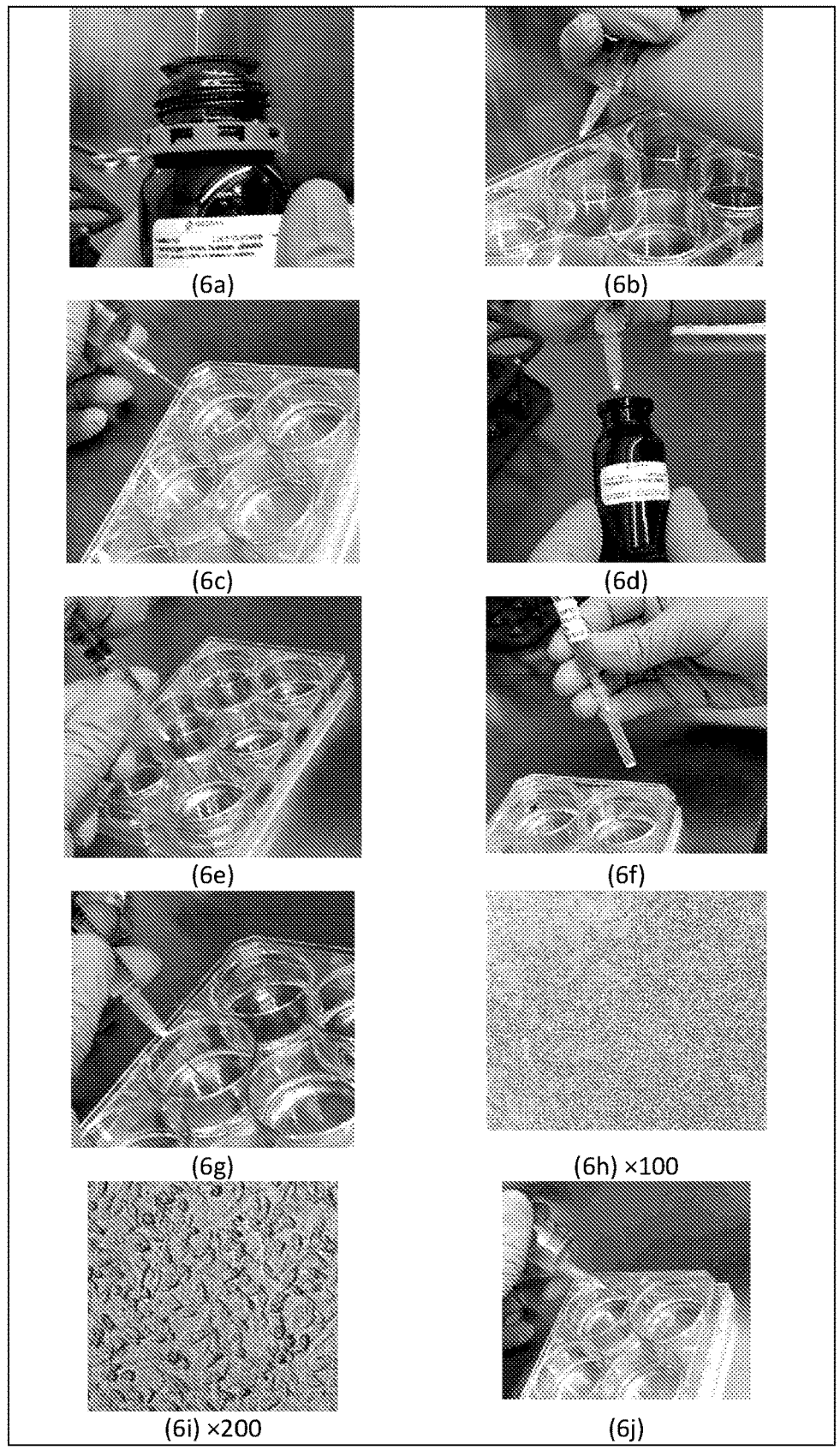
FIG. 6 demonstrates the first mode of primary hair follicles production by serial seeding on fibrin gel (the gel contains an extract of fetal hair follicle cells with growth factors) mesenchymal stem cells of the patient's hair follicles and the scalp skin cells of the patient: (6a)—Preparation of the fibrinogen solution in the DMEM; (6b)—Bottling of the fibrinogen solution in the wells of the cell culture plate; (6c) Adding extract of fetal hair follicles cells with growth factors; (6d) Preparation of thrombin solution in DMEM; (6e) Adding thrombin solution to the wells for fibrin gel forming; (6f) Mesenchymal stem cells of the patient's hair follicles; (6g) Seeding mesenchymal stem cells of the patient's hair follicles on a gel; (6h) Micro photo of mesenchymal stem cells of the patient's hair follicles after seeding on the gel; (6i) Micro photo of skin cells of the patient's scalp in culture; (6j) Seeding the patient's scalp skin cells onto the mesenchymal stem cells of the patient's hair follicles.
Figure 7:
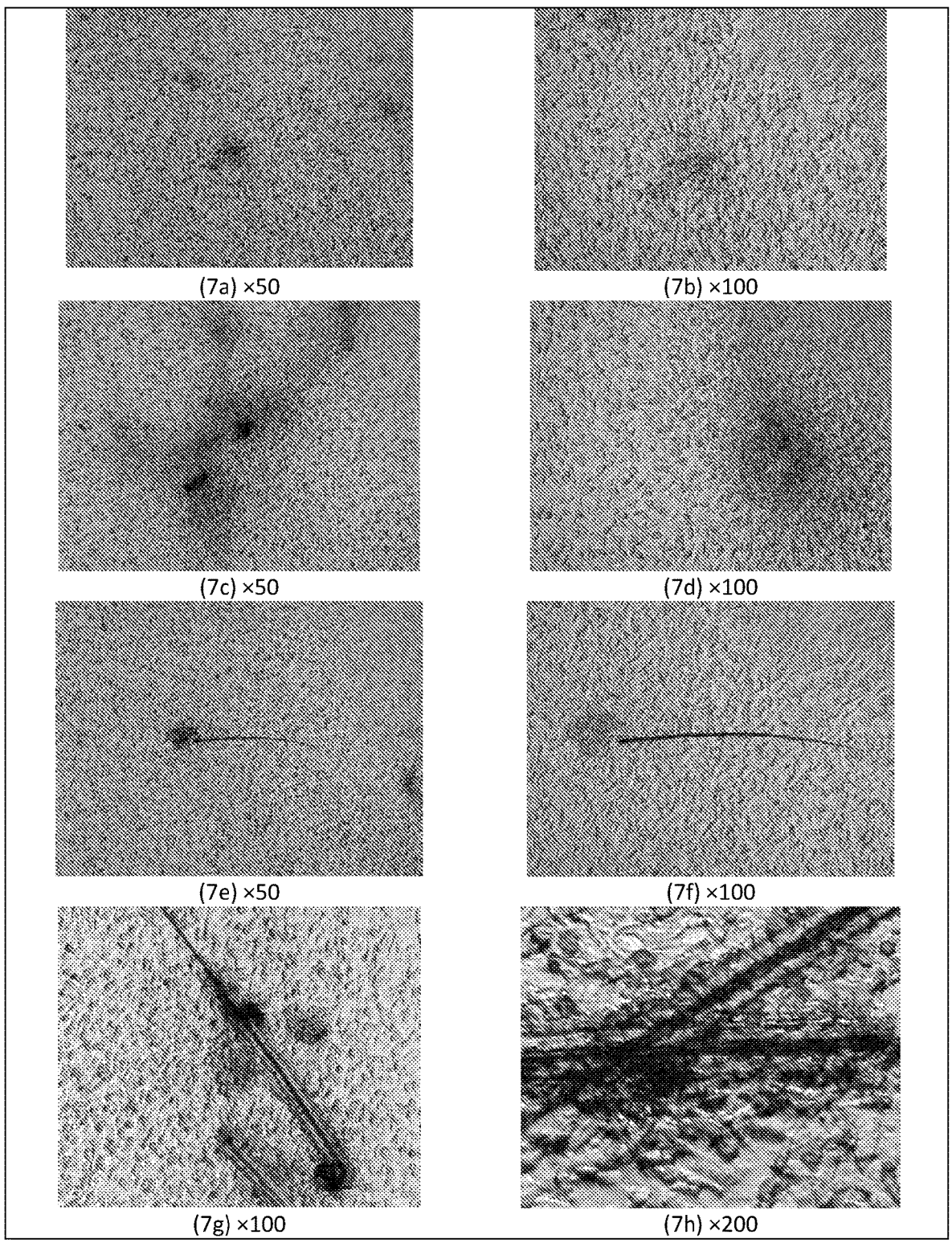
FIG. 7 shows the formation of primary hair follicles in the wells of cell culture plate: (7a, 7b) Formation of clusters of cells on the surface of the gel; (7c, 7d)—The appearance of a dense aggregation of dark cells in the center of the cell cluster (germ of the primary hair follicle); (7e, 7f)—Hair growth from the follicle, which is localized inside the gel; (7g, 7h) Primary hair follicles on the surface of the gel.

Growth of patient-donor primary hair follicles after serial seeding on fibrin gel (the gel contains an extract of fetal hair follicle cells with growth factors) mesenchymal stem cells of the patient's hair follicles and the scalp skin cells of the patient (2D-cultivation). Step 1. Preparation of fibrin gel: 10 ml DMEM bottling in the wells of the cell culture plate; human lyophilized fibrinogen dissolves in DMEM (FIG. 6a); fibrinogen solution bottling in the wells of the cell culture plate (final fibrinogen concentration 3.0 g/L) (FIG. 6b). Step 2. Adding to DMEM 2 ml extract of fetal hair follicles cells with growth factors (FIG. 6c). Step 3. Creation of fibrin gel: preparation of thrombin solution in DMEM (FIG. 6d); adding thrombin solution (30 NIH Unit) to the wells for fibrin gel forming (FIG. 6e). Step 4. Sandwich seeding of patient-donor cells on fibrin gel: mesenchymal stem cells of the patient's hair follicles (FIG. 6f); seeding mesenchymal stem cells of the patient's hair follicles on a gel (FIG. 6g); micro photo of mesenchymal stem cells of the patient's hair follicles after seeding on the gel (FIG. 6h); micro photo of skin cells of the patient's scalp in culture (FIG. 6i); seeding the patient's scalp skin cells onto the mesenchymal stem cells of the patient's hair follicles (FIG. 6j). During 6 weeks after cells seeding observed the formation of primary hair follicles in the wells of cell culture plate: formation of clusters of cells on the surface of the gel (FIG. 7a, FIG. 7b); the appearance of a dense aggregation of dark cells in the center of the cell cluster (germ of the primary hair follicle) (FIG. 7c, FIG. 7d); hair growth from the follicle, which is localized inside the gel (FIG. 7e, FIG. 7f); primary hair follicles on the surface of the gel (FIG. 7g, FIG. 7h).

Figure 8:
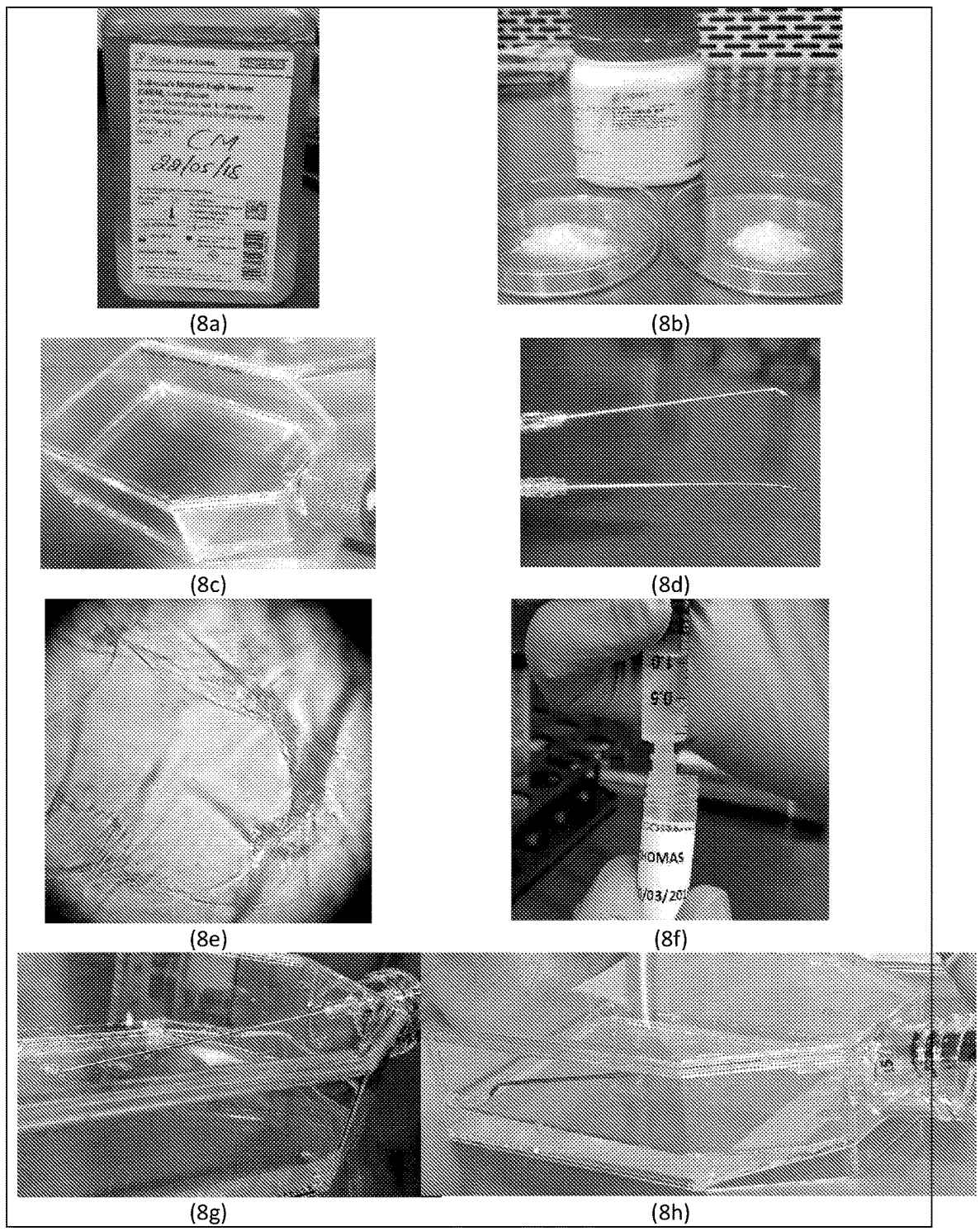
FIG. 8 demonstrates the second mode of primary hair follicles production by serial seeding inside the fibrin gel (the gel contains an extract of fetal hair follicle cells with growth factors) mesenchymal stem cells of the patient's hair follicles and the scalp skin cells of the patient: (8a)—Cultivation medium with fetal follicle cell extract and fibrinogen; (8b)—Additionally, epsilon-aminocaproic acid is added to DMEM to inhibit fibrinolysis; (8c)—Fibrin gel, which is formed in the flask after the addition of thrombin; (8d)—Needles for seeding cells inside the gel; (8e)—Empty hole after needle puncture of the gel; (8f)—Mesenchymal stem cells of the patient's hair follicles; (8g)—Seeding the patient's hair follicles mesenchymal stem cells inside the gel; (8*h*)—Seeding skin cells of the patient's scalp on the mesenchymal stem cells of his hair follicles ("sandwich" method).

Growth of patient-donor primary hair follicles after serial seeding into fibrin gel (the gel contains an extract of fetal hair follicle cells with growth factors) mesenchymal stem cells of the patient's hair follicles and the scalp skin cells of the patient (3D-cultivation). Step 1. Preparation of fibrin gel: 30 ml DMEM which contain extract of fetal hair follicle cells with growth factors and fibrinogen in 3.0 g/L final concentration (FIG. 8a) bottling into the T75 flask; adding into flask epsilon-aminocaproic acid in final concentration 30.0 g/L (FIG. 8b); after adding thrombin solution (100 NIH Unit) into the flask fibrin gel forming (FIG. 8c). Step 2. Procedure of cells seeding into fibrin gel: special needles for seeding cells inside the gel (FIG. 8d); empty hole after needle puncture of the gel (FIG. 8e); mesenchymal stem cells of the patient's hair follicles (FIG. 8f); seeding the patient's hair follicles mesenchymal stem cells inside the gel (FIG. 8g); seeding skin cells of the patient's scalp on the mesenchymal stem cells of his hair follicles (3D "sandwich" method) (FIG. 8h).

Figure 9:
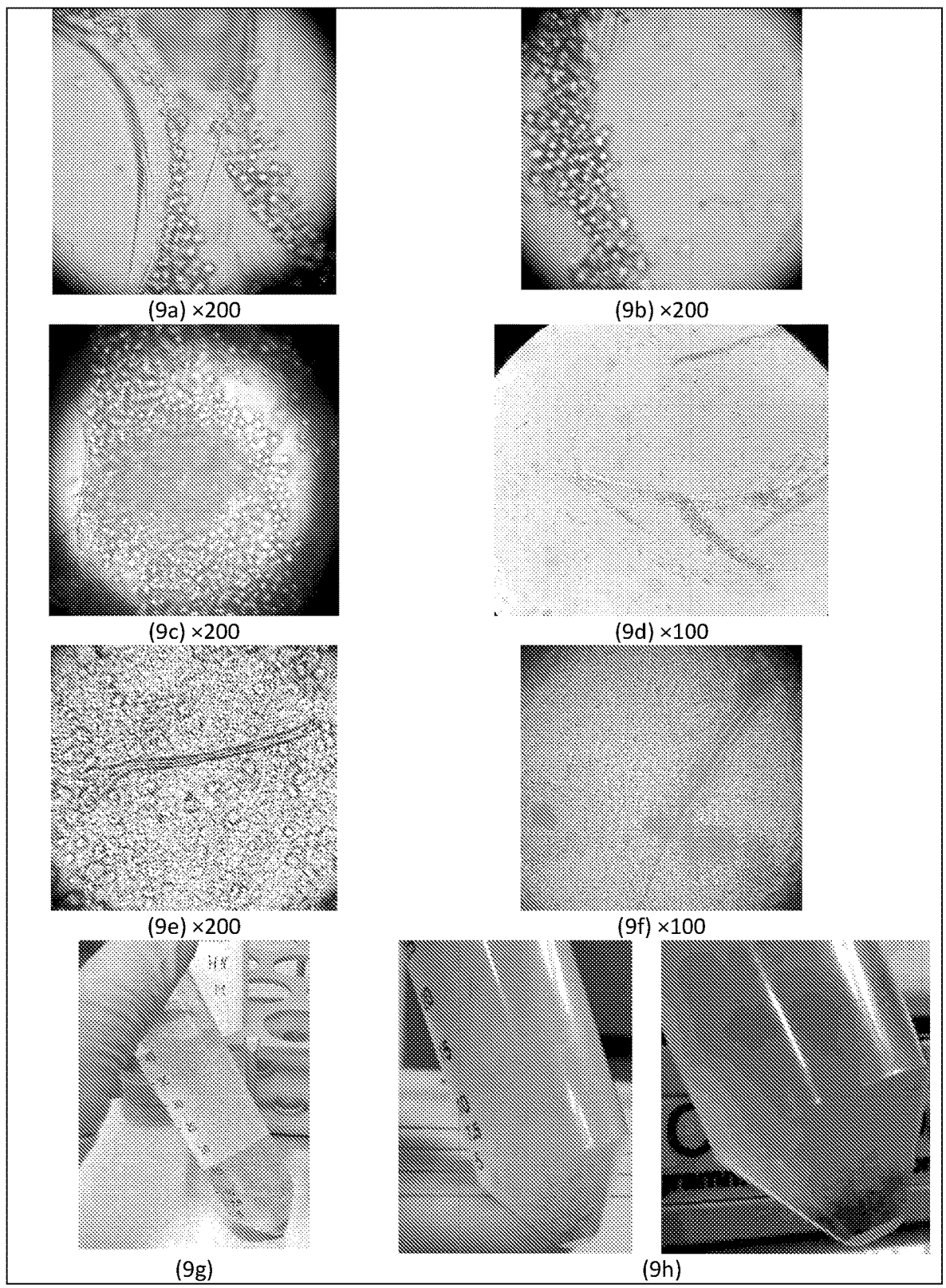
FIG. 9 demonstrates the formation and development of a patient's primary hair follicles inside the fibrin gel that contains growth factors of fetal hair follicle cells: (9*a*)—Mesenchymal stem cells of hair follicles and scalp skin cells of a patient in a gel hole; (9*b*)—Migration of mesenchymal stem cells of hair follicles and skin cells of the patient's scalp into the walls of the gel hole; (9*c*)—Clustering of cells inside the fibrin gel after 72 hours of incubation; (9*d*)—The appearance of primordia of the primary hair follicles in the fibrin gel; (9*e*)—Development of primary hair follicles in the fibrin gel; (9*f*)—Primary hair follicle in fibrin gel; (9*g*)—Separation of the primary hair follicles by centrifuging: the top layer is the DMEM, the middle one is the fibrin gel, the bottom is the follicles; (9*h*)—Follicle separation by the method of self-precipitation after the fibrin gel is dissolved by plasmin.

During 5-6 weeks after cells seeding observed the formation and development of a patient's primary hair follicles inside the fibrin gel that contains growth factors of fetal hair follicle cells: mesenchymal stem cells of hair follicles and scalp skin cells of a patient in a gel hole (FIG. 9a); migration of mesenchymal stem cells of hair follicles and skin cells of the patient's scalp into the walls of the gel hole (FIG. 9b); clustering of cells inside the fibrin gel after 72 hours of incubation (FIG. 9c); the appearance of primordia of the primary hair follicles in the fibrin gel (FIG. 9d); development of primary hair follicles in the fibrin gel (FIG. 9e); primary hair follicle in fibrin gel (FIG. 9f); separation of the primary hair follicles by centrifuging: the top layer is the DMEM, the middle one is the fibrin gel, the bottom is the follicles (FIG. 9g); follicle separation by the method of self-precipitation after the fibrin gel is dissolved by plasmin (FIG. 9h).

EXAMPLES

Example 1

Figure 10:
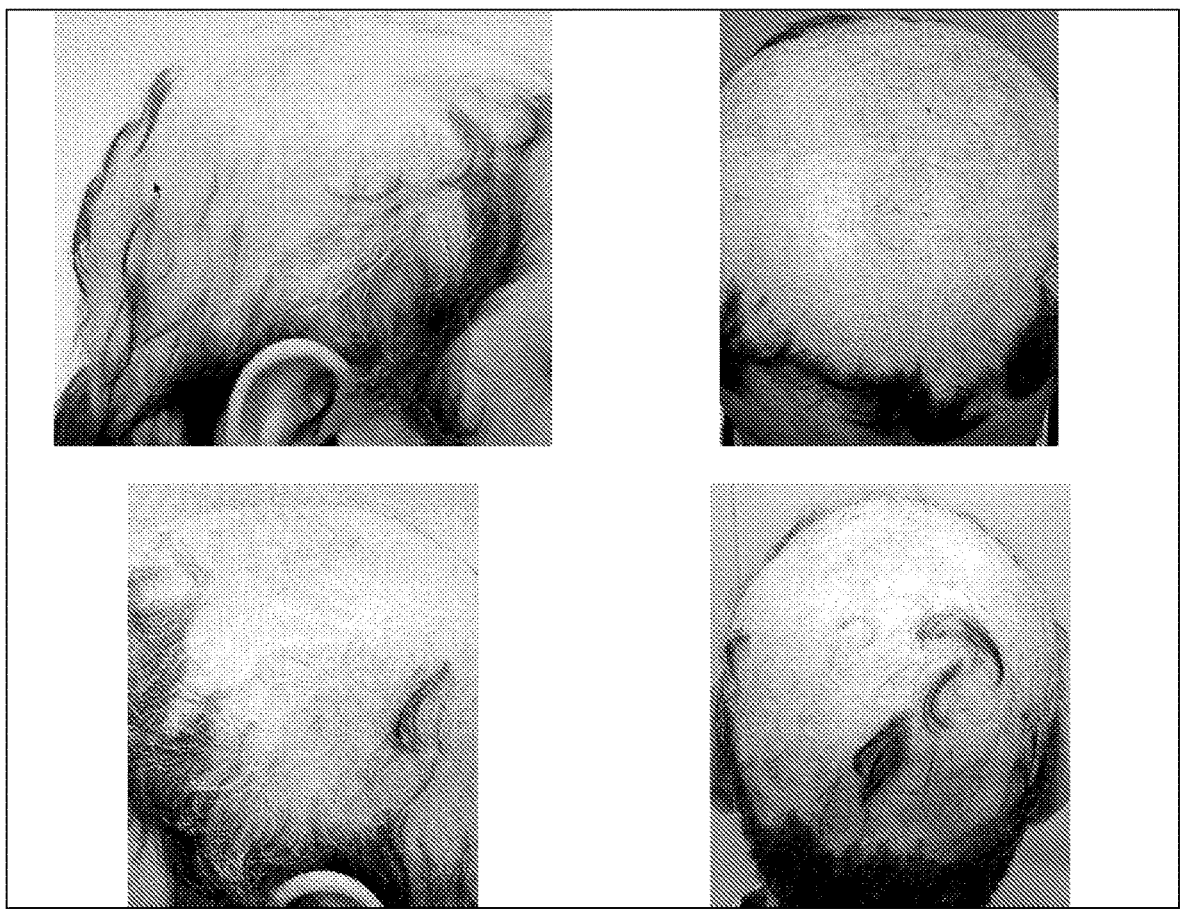
FIG. 10 illustrates Example 1: Patient X with a chemical burn of the scalp donor of occipital hair follicles for stem cell isolation.
Figure 11:
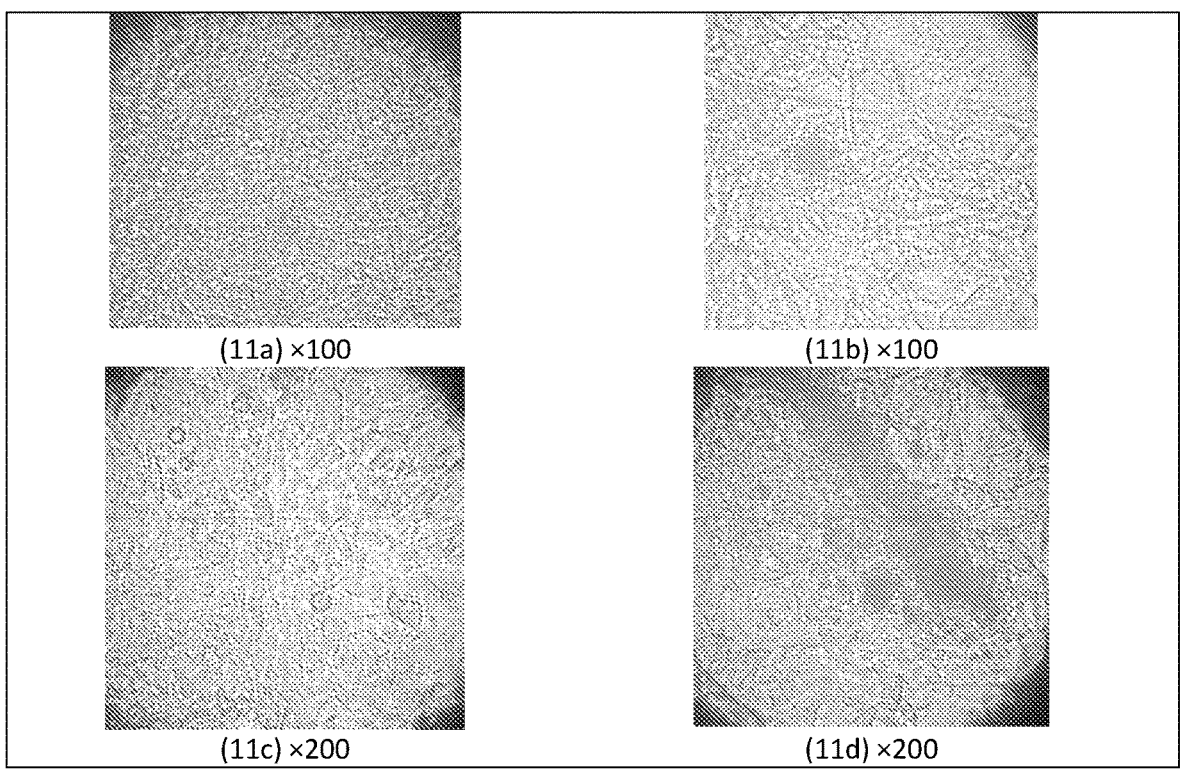
FIG. 11 shows the formation of primary hair follicles from mesenchymal stem cells and scalp skin cells of patient X in a fibrin gel without adding the growth factors of fetal hair follicles into the gel (11*a*, 11*c* control), and in case of adding the growth factors of fetal hair follicles into the gel (11*b*, 11*d* experiment): in the control the germs of the hair follicles is not formed (11*a*) and the growth of the primary hair follicles is not observed (11*c*), while in the fibrin gel that contains growth factors of fetal hair follicle formed germ (11*b*), from which then grows primary hair follicle (11*d*).
Figure 12:
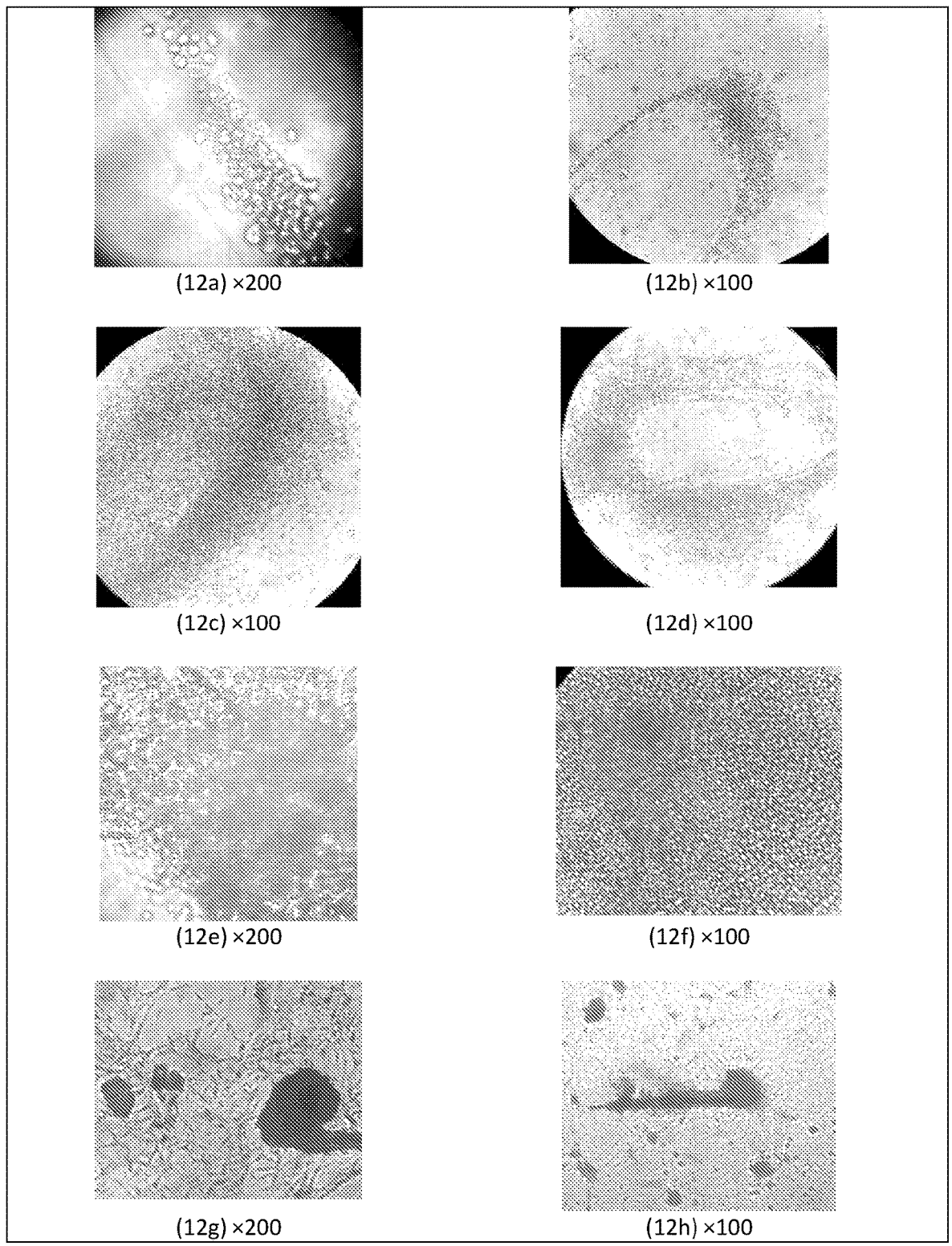
FIG. 12 shows the main stages of the primary hair follicles formation from mesenchymal stem cells of hair follicles and scalp skin cells of patient-donor X into fibrin gel which contain the growth factors of fetal hair follicles cells: (12*a*)—Mesenchymal stem cells of hair follicles and skin of the scalp of patient-donor X immediately after sinking into the fibrin gel; (12*b*)—Expansion and migration of patient-donor X cells into the gel with the formation of clusters and the appearance of dark cells; (12*c*) Formation of dark cell clusters in the gel; (12*d*, 12*e*, 12*f*)—Formation of the germs of the primary hair follicle; (12*g*)—Growth of primary hair follicles and scalp skin fibroblasts; (12*h*)—Primary hair follicles with radially growing fibroblasts of the patient's scalp skin.

Patient X—donor of hair follicles. Diagnosis: a chemical burn of the scalp, subtotal alopecia (FIG. 10). To assess the importance of the presence of fetal hair follicles growth factors in fibrin gel, special studies have been carried out. Patient X hair follicles mesenchymal stem cells and cells of scalp skin were cultured inside a fibrin gel without growth factors of fetal hair follicle cells (control) and in the gel that contained these growth factors (experiment), In the control the germs of the hair follicles are not formed (FIG. 11a) and the growth of the primary hair follicles is not observed (FIG. 11c), while in the fibrin gel that contains growth factors of fetal hair follicle formed germ (FIG. 11b), from which then grows primary hair follicle (FIG. 11d). The main stages of the primary hair follicles formation from mesenchymal stem cells of hair follicles and scalp skin cells of patient-donor X into fibrin gel which contain the growth factors of fetal hair follicles cells: mesenchymal stem cells of hair follicles and skin of the scalp of patient-donor X immediately after sinking into the fibrin gel (FIG. 12a); expansion and migration of patient-donor X cells into the gel with the formation of clusters and the appearance of dark cells (FIG. 12b); formation of dark cell clusters in the gel (FIG. 12c); formation of the germs of the primary hair follicle (FIG. 12d, FIG. 12e, FIG. 12f); growth of primary hair follicles and scalp skin fibroblasts (FIG. 12g); primary hair follicles with radially growing fibroblasts of the patient's scalp skin (FIG. 12h).

Example 2

Figure 13:
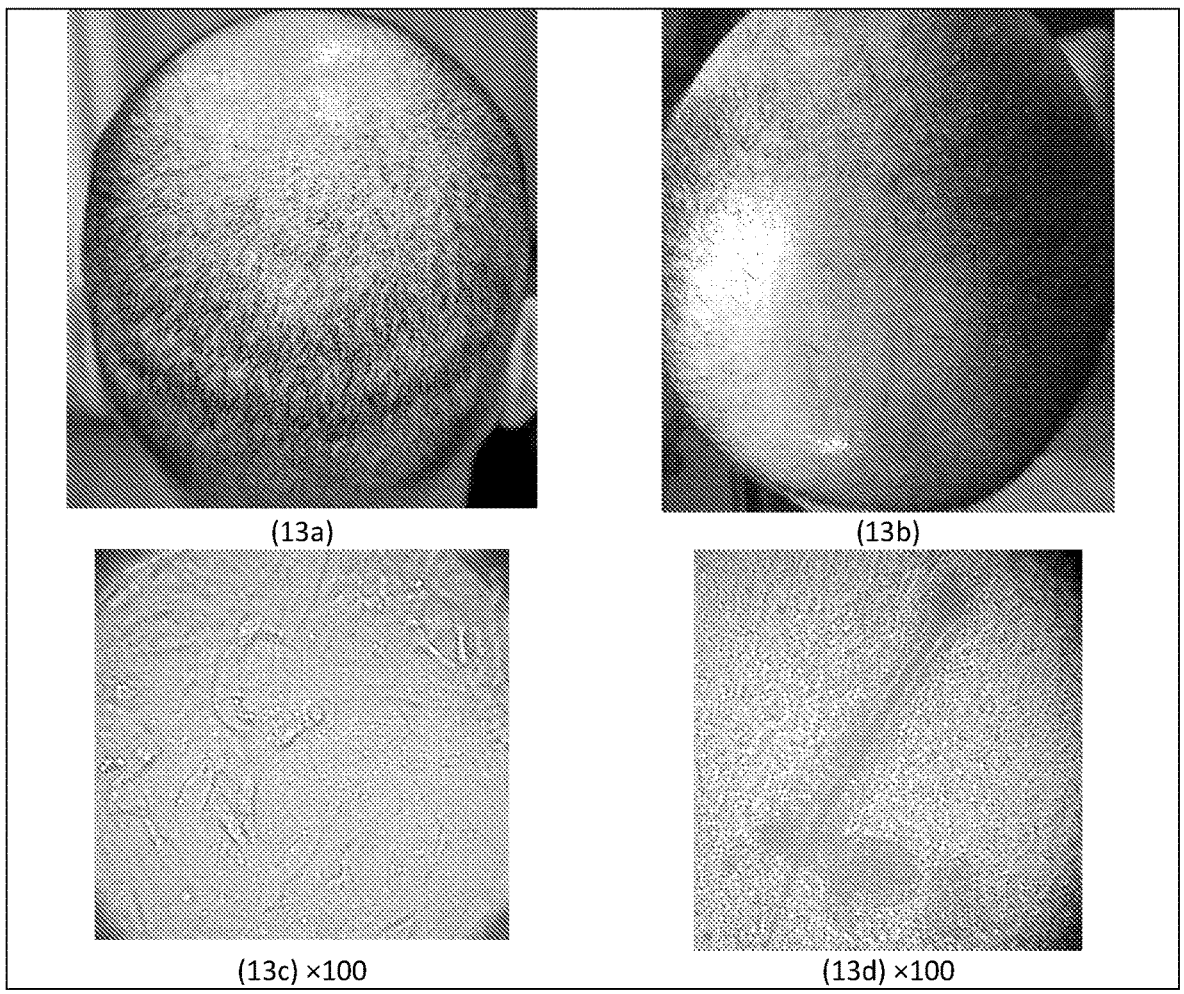
FIG. 13 illustrates Example 2: patient Y with androgenic alopecia—donor of occipital hair follicles for stem cell isolation (13*a*, 13*b*), and shows the formation of primary hair follicles from mesenchymal stem cells and scalp skin cells of patient Y in a fibrin gel without adding the growth factors of fetal hair follicles into the gel (13*c* control), and in case of adding the growth factors of fetal hair follicles into the gel (13*d* experiment); in the control the growth of the primary hair follicles is not observed (13*c*), while in the fibrin gel that contains growth factors of fetal hair follicle formed primary hair follicle occurred (13*d*).
Figure 14:
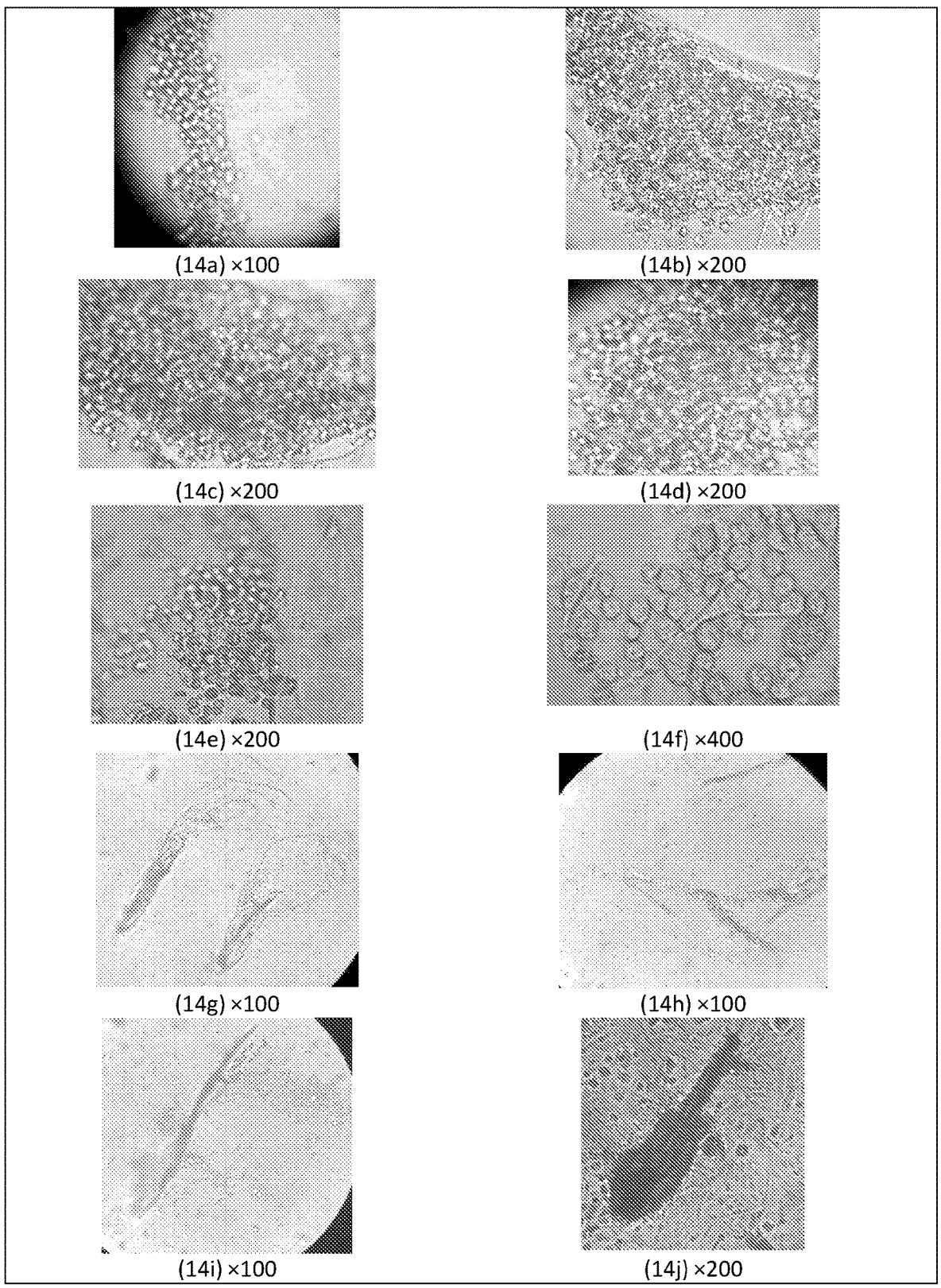
FIG. 14 shows the main stages of the primary hair follicles formation from mesenchymal stem cells of hair follicles and scalp skin cells of patient-donor Y into fibrin gel which contain the growth factors of fetal hair follicles cells: (14*a*)—Mesenchymal stem cells of hair follicles and skin of the scalp of patient-donor Y immediately after sinking into the fibrin gel; (14*b*)—Expansion and migration of patient-donor Y cells into the gel with the formation of clusters and the appearance of dark cells; (14*c*, 14*d*, 14*e*)—Formation of dark cell clusters in the gel; (14*e*, 14*f*)—Appearance of myelocytes; (14*g*, 14*h*)—Formation of the germs of the primary hair follicle; (14*i*)—Growth of primary hair follicles; (14*j*)—Primary hair follicles with radially growing fibroblasts of the patient's scalp skin.

Patient Y—donor of hair follicles. Diagnosis: androgenic alopecia (FIG. 13a, FIG. 13b). To assess the importance of the presence of fetal hair follicles growth factors in fibrin gel, special studies have been carried out. Patient Y hair follicles mesenchymal stem cells and cells of scalp skin were cultured inside a fibrin gel without growth factors of fetal hair follicle cells (control) and in the gel that contained these growth factors (experiment). In the control the growth of the primary hair follicles is not observed (FIG. 13c), while in the fibrin gel that contains growth factors of fetal hair follicle grows of patient Y primary hair follicle occurred (FIG. 13d). The main stages of the primary hair follicles formation from mesenchymal stem cells of hair follicles and scalp skin cells of patient-donor Y into fibrin gel which contain the growth factors of fetal hair follicles cells: mesenchymal stem cells of hair follicles and skin of the scalp of patient-donor Y immediately after sinking into the fibrin gel (FIG. 14a); expansion and migration of patient-donor Y cells into the gel with the formation of clusters and the appearance of dark cells (FIG. 14b); formation of dark cell clusters in the gel (FIG. 14c, FIG. 14d, FIG. 14e); appearance of myelocytes (FIG. 14e, FIG. 14f); formation of the germs of the primary hair follicle (FIG. 14g, FIG. 14h); growth of primary hair follicles (FIG. 14i); primary hair follicles with radially growing fibroblasts of the patient's scalp skin (FIG. 14j).

Example 3

Figure 15:
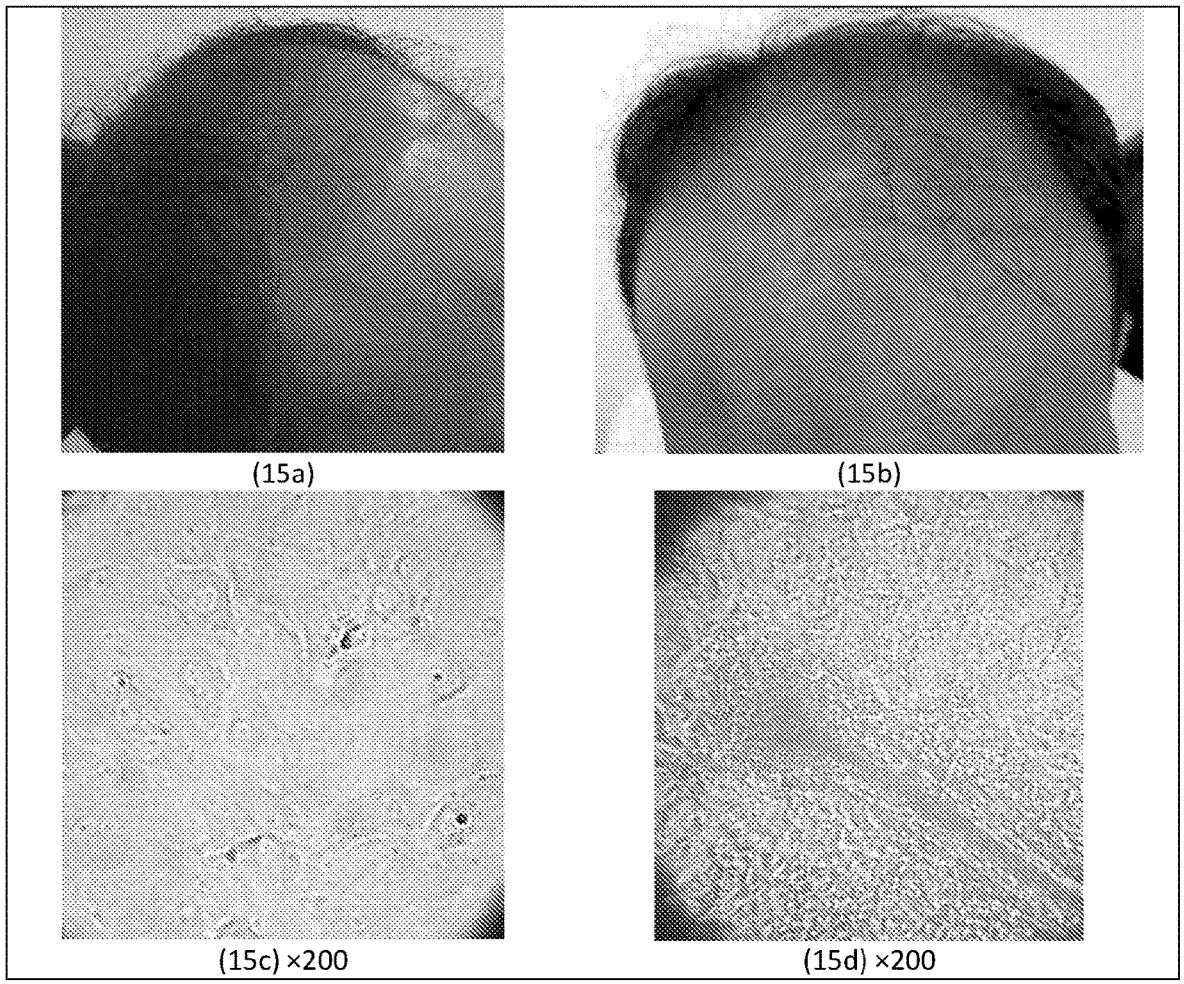
FIG. 15 illustrates Example 3: patient Z with androgenic alopecia—donor of occipital hair follicles for stem cell isolation (15*a*, 15*b*), and shows the formation of primary hair follicles from mesenchymal stem cells and scalp skin cells of patient Z in a fibrin gel without adding the growth factors of fetal hair follicles into the gel (15*c*—control), and in case of adding the growth factors of fetal hair follicles into the gel (15*d*—experiment); in the control the growth of the primary hair follicles is not observed (15*c*), while in the fibrin gel that contains growth factors of fetal hair follicle formed primary hair follicle occurred (15*d*).
Figure 16:
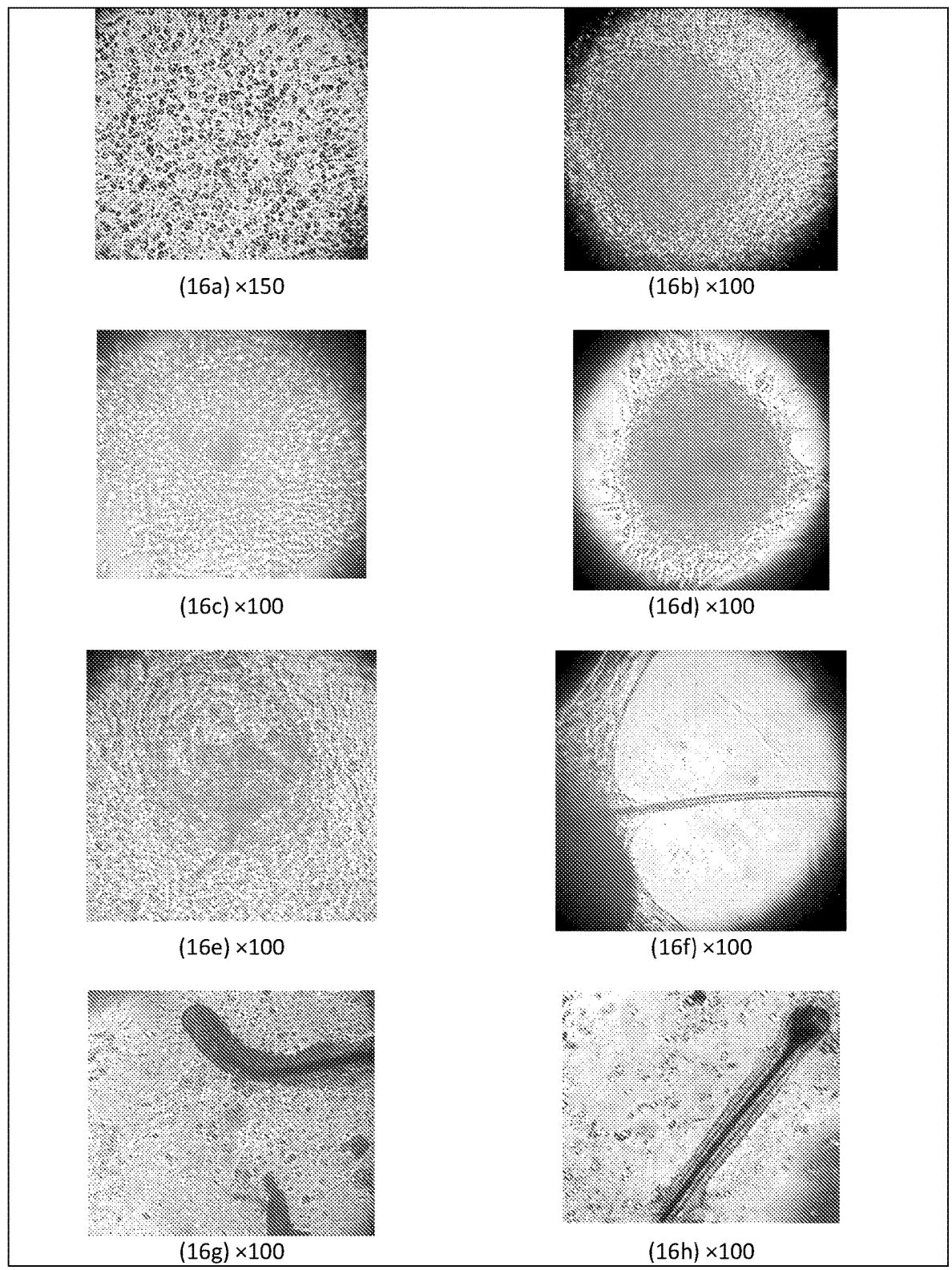
FIG. 16 shows the main stages of the primary hair follicles formation from mesenchymal stem cells of hair follicles and scalp skin cells of patient-donor Z into fibrin gel which contain the growth factors of fetal hair follicles cells: (16*a*)—Mesenchymal stem cells of hair follicles and skin of the scalp of patient-donor Z one day after sinking into the fibrin gel; (16*b*)—Expansion and migration of patient-donor Z cells into the gel with the formation of clusters and the appearance of dark cells; (16*c*)—Formation of dark cell clusters in the gel; (16*d*)—Growth of scalp skin fibroblasts around the primary follicle germ; (16*e*)—Formation of the germs of the primary hair follicle; (16*f*)—Hair growth and growth of skin cells around the primary follicle; (16*g*) Growth of primary hair follicles and skin fibroblasts; (16*h*)—Primary hair follicle.

Patient Z—donor of hair follicles. Diagnosis: androgenic alopecia (FIG. 15a, FIG. 15b). To assess the importance of the presence of fetal hair follicles growth factors in fibrin gel, special studies have been carried out. Patient Z hair follicles mesenchymal stem cells and cells of scalp skin were cultured inside a fibrin gel without growth factors of fetal hair follicle cells (control) and in the gel that contained these growth factors (experiment). In the control the growth of the primary hair follicles is not observed (FIG. 15c), while in the fibrin gel that contains growth factors of fetal hair follicle grows of patient Z primary hair follicle occurred (FIG. 15d). The main stages of the primary hair follicles formation from mesenchymal stem cells of hair follicles and scalp skin cells of patient-donor Z into fibrin gel which contain the growth factors of fetal hair follicles cells: mesenchymal stem cells of hair follicles and skin of the scalp of patient-donor Z one day after sinking into the fibrin gel (FIG. 16a); expansion and migration of patient-donor Z cells into the gel with the formation of clusters and the appearance of dark cells (FIG. 16b); formation of dark cell clusters in the gel (FIG. 16c); growth of scalp skin fibroblasts around the primary follicle germ (FIG. 16d); formation of the germs of the primary hair follicle (FIG. 16e); hair growth and growth of skin cells around the primary follicle (FIG. 16f); growth of primary hair follicles and skin fibroblasts (FIG. 16g); primary hair follicle (FIG. 16h).

The invention claimed is:

1. A method for creating de novo autologous primary hair follicles in 3D culture by recreating the conditions of embryogenesis of primary hair follicles, which involves: isolating mesenchymal stem cells of donor hair follicles and their expansion; isolating of donor scalp skin cells and their temporary cryopreservation; seeding, using a sandwich method, mesenchymal stem cells of the donor's hair follicles and skin cells of the donor's scalp in a monolayer of fibrin gel based on a nutrient medium containing growth factors of fetal scalp hair follicles; lysing of the fibrin gel monolayer with exogenous plasmin; isolating de novo-formed primary donor hair follicles from a lysed fibrin gel monolayer by self-precipitation; washing the de novo-formed primary hair follicles of the donor with phosphate buffer; transplanting of de novo-formed primary hair follicles to a donor.

2. The method for creating de novo autologous primary hair follicles according to claim 1, wherein:
    (i) extraction of hair follicles from the donor's scalp is performed by simultaneously collecting two follicular units with small (1-2 mm$^3$) pieces of donor scalp skin located between them;
    (ii) isolation of mesenchymal stem cells of the donor's hair follicles and their expansion in 2D culture is carried out using standard procedures and standard reagents by separation of adhesive mesenchymal cells of the donor's scalp hair follicles after achieving 70-80% confluency;
    (iii) the method of preparation of autologous primary hair follicles according to (i), wherein isolation of donor scalp skin cells is carried out by soft homogenization of the donor scalp skin located between the extracted hair follicles in order to create a cell suspension containing interfollicular stem/progenitor cells of the donors' skin;
    (iv) the method of preparation of autologous primary hair follicles according to (iii), wherein temporary preservation of donor scalp skin cells suspension that contains interfollicular stem/progenitor cells of the donors' skin is performed by programmable cryopreservation in liquid nitrogen according to a standard procedure with the aim of temporarily preserving this cell suspension for 2-3 weeks—the period which necessary for the expansion of mesenchymal stem cells of the donor's scalp hair follicles; and defrosting of a suspension of skin cells from the donor's scalp is carried out according to a standard procedure.

3. The method for creating de novo autologous primary hair follicles according to claim 1, wherein seeding using a standard sandwich method of mesenchymal stem cells of the donor's scalp hair follicles and a suspension of donor scalp skin cells for 3D cultivation is carried out in a monolayer of fibrin gel based on a nutrient medium containing growth factors of the fetal scalp skin hair follicles of a fetus of 18-20 weeks of gestation obtained as a result of medical termination pregnancy independent of the researcher.

4. The method for creating de novo of autologous primary hair follicles according to claim 3, wherein fetal growth factors are extracted by gently homogenizing the primary hair follicles of the fetal scalp, and followed centrifugation and filtration of the resulting supernatant.

5. The method for creating de novo autologous primary hair follicles according to claim 3, wherein the growth factors and concentrations of the growth factors of the fetal scalp skin hair follicles: HGF-43.91±11.84 pg/ml; IGF-1-432.6±65.76 pg/ml; VEGF-26.55±10.43 pg/ml; FGF-7-121.90±37.10 pg/ml; EGF-2.82±0.92 pg/ml; SCF-440.70±19.52 pg/ml; TGFβ1-82.13±1.38 pg/ml; TNFα-249.53±10.40 pg/ml; ANGPT1-12970.00±1062.39 pg/ml; bFGF-9540.00±674.25 pg/ml; VEGF-A-5360.00±381.13 pg/ml.

6. The method for creating de novo autologous primary hair follicles according to claim 4, wherein biosafety control of fetal scalp primary hair follicles growth factors is carried out according to generally accepted guidelines developed for regenerative medicine.

7. The method for creating de novo autologous primary hair follicles according to claim 1, wherein lysis of the fibrin gel monolayer after de novo formation primary hair follicles is performed by exogenous plasmin at a concentration not less then 1.0 mg/ml.

8. The method for creating de novo autologous primary hair follicles according to claim 1, wherein isolation of de novo primary donor's hair follicles from a lysed fibrin gel monolayer is performed by self-precipitation.

9. The method for creating de novo autologous primary hair follicles according to claim 1, wherein washing of the de novo formed primary hair follicles of the donor is carried out three times with phosphate buffer in order to clean the primary hair follicles from impurities of plasmin, fibrin-degradation products and the cultivation medium.

10. The method for creating de novo autologous primary hair follicles according to claim 1, wherein transplantation of de novo-formed primary hair follicles to a donor is carried out according to a standard method in cases where the hair follicles on the bald skin of the donor's scalp are dead and are not subject to stimulating growth such as chemical burns, toxic, hormonal and other factors that lead to persistent alopecia due to complete destruction of hair follicles.

* * * * *